United States Patent [19]

Valentine et al.

[11] Patent Number: 5,037,419

[45] Date of Patent: Aug. 6, 1991

[54] BLOOD BAG SYSTEM CONTAINING VITAMIN E

[75] Inventors: David L. Valentine; Andreas M. Papas, both of Kingsport; Edward T. Ostermeyer, Johnson City; James E. Huffaker; Eileen M. Taggart, both of Kingsport, all of Tenn.

[73] Assignee: Eastman Kodak Company, Rochester, N.Y.

[21] Appl. No.: 410,205

[22] Filed: Sep. 21, 1989

[51] Int. Cl.$^5$ .............................................. A61M 5/00
[52] U.S. Cl. .................................... 604/408; 604/403; 604/4
[58] Field of Search .............................. 604/403–410, 604/4–6

[56] References Cited

U.S. PATENT DOCUMENTS

| 4,496,361 | 1/1985 | Kilkson | 604/408 |
| 4,657,542 | 4/1987 | Ohachi | 604/410 |
| 4,880,425 | 11/1989 | Kuhlemann et al. | 604/404 |

Primary Examiner—Robert A. Hafer
Assistant Examiner—Kerry Owens
Attorney, Agent, or Firm—Mark A. Montgomery; William P. Heath, Jr.

[57] ABSTRACT

The present invention discloses a blood bag system that avoids the requirements of a plasticizer that is extractable by blood or blood components. The blood bag is made of a certain plastic material having particular properties including sufficient oxygen and carbon dioxide permeabilities. The blood bag also contains an effective amount of vitamin E.

20 Claims, No Drawings 5,037,419

BLOOD BAG SYSTEM CONTAINING VITAMIN E

This invention relates to blood bag systems and blood storage.

BACKGROUND OF THE INVENTION

Single and multiple blood bags are currently commercially available for storing whole blood and fractions thereof. Most of these blood bags are made of polyvinylchloride (PVC) plasticized with di-2-ethylhexylphthalate (DEHP, also known as dioctyl phthalate or DOP). Plasticizers such as DOP are an essential component of these and other blood bags. (See U.S. Pat. Nos. 4,451,259; 4,286,597; 4,300,559, 4,301,800; 4,507,387; 4,222,379). The use of a plasticizer in the plastic material was needed in order to make the PVC material sufficiently flexible to be made into bags; it was later found, however, that DOP was also needed to increase the storage life of blood to acceptable levels and somehow interacted with the blood. Containers made of a plastic material without a plasticizer caused blood stored in such containers, under the usual blood storage conditions, to exhibit an undesirably high plasma hemoglobin content, indicating that the rate of red blood cell lysis was high.

Many physicians and other interested parties have expressed concern over inclusion of a plasticizer in blood bags (see, for example, *Report to the U.S. Consumer Product Safety Commission* by the Chronic Hazard Advisory Panel on di(2-ethylhexyl) phthalate (DEHP). U.S. Consumer Product Safety Commission Directorate for Health Sciences, Washington, September 1985, and *Journal of The American Association of Blood Banks*, May, 1989, Vol. 29, No. 4, pp 287–297). The plasticizer in blood bags is blood extractable, i.e. extractable from the plastic material into the blood. The extracted plasticizer enters the human body along with the blood during infusion and could be significantly detrimental to the health of the body, particularly if there is an allergic reaction or if the plasticizer is built up over numerous infusions.

Attempts have been made to prepare blood bag materials without the use of a plasticizer. (See U.S. Pat. No. 4,301,800). These attempts were generally unsuccessful and resulted in an unacceptably high level of blood cell lysis when used for blood storage materials. Therefore, it would be desirable to have an acceptable blood bag system which does not require the presence of a plasticizer but yet is compatible with stored blood and its components, i.e., does not result in an undesirably high red blood cell lysis when storing red blood cells. Vitamin E has been shown in some instances to have beneficial effects on blood. (See, for example, S. Luczek and F. Wolf, *German Medical Monthly*, Vol. VIII, No. 5, Stuttgart, May 1963, pp. 182–185; I. Kurokawa et al., *Vitamins* (Japan) 39, (2), 1969, pp. 86–90; I. Kurokawa et al., *Vitamins* (Japan) 40, (3), 1969 pp. 206–209; and I. Kurokawa et al., *The Journal of Vitaminology*, 16, 1970 pp. 180–189).

SUMMARY OF THE INVENTION

It has been unexpectedly found that a suitable blood bag system can be made using vitamin E in combination with a flexible plastic material essentially free of blood extractables such as plasticizers.

In accordance with the present invention there is provided a blood bag comprising: an effective blood stabilizing amount of vitamin E; and a flexible, transparent, hemocompatible, sterilizable, smooth, inert plastic material having sufficient oxygen and carbon dioxide permeabilities to be effective as a blood storage bag and maintain the useful life of stored blood and its components.

There is also provided a method for storing blood or at least one blood fraction which comprises placing said blood or blood fraction in the blood bag of this invention.

We have discovered that the effects of vitamin E on the stability of blood subjected to long term storage varies considerably depending upon the type and thickness of material which is used to make the container for storing the blood. We have also found differences in activity among the various forms of vitamin E on the stability of blood in storage which have heretofore been unknown.

Based on our findings, we have developed a novel blood bag system that is acceptable and meets the long-felt need in the art of a system substantially free of harmful extractables such as plasticizers.

DETAILED DESCRIPTION OF THE INVENTION

It has been found that acceptable stability of blood stored in blood bags can be achieved with an effective amount of vitamin E if the plastic material forming the blood bag is essentially free of harmful blood extractables, flexible, hemocompatible, sterilizable and has sufficient oxygen and carbon dioxide permeabilities.

It is preferred that this plastic material have an oxygen permeability of at least about 100 PU; and a carbon dioxide permeability of at least about 800 PU. It is more preferred that this plastic material have an oxygen permeability of at least about 250 PU and a carbon dioxide permeability of at least about 2,500 PU. PU means permeability units in cc(STP)·mil/100 square inches·day·atm. STP=standard temperature and pressure; mil=0.001 inches; and atm=pressure of 1.0 atmosphere.

The oxygen and carbon dioxide permeabilities of a given plastic material depend greatly upon the chemical nature of the material. In addition, the oxygen and carbon dioxide permeabilities of these materials generally vary proportionally with the thickness of the material i.e. the thicker the material the lower the permeability. At present there are no real upperlimits to the oxygen and carbon dioxide permeabilities and thus it is preferred that the plastic material be as thin as possible but yet sufficiently thick so as to maintain its integrity and not fail during use. Therefore, while having sufficient oxygen and carbon dioxide permeabilities it is also preferred that the plastic material forming the blood bag have a plastic thickness between about 2 and 60 mils, preferably between about 5 and 40 mils. Blood cells need good dissolved gas exchange and thus need to be stored in blood bags with higher oxygen and carbon dioxide permeabilities. Therefore, when storing blood products that contain red blood cells, or platelets, the preferred thickness of the plastic material is between about 3 and 15 mils. More preferably, the thickness of the plastic material is between about 5 and 10 mils with about 5 mil being most preferred.

The plastic material of the present invention should also have other characteristics if it is to be a commercially acceptable blood bag. The blood bag must then be flexible, hemocompatible, and sterilizable. In addition, it is desirable that the blood bag be smooth, translucent or transparent, and inert.

By "flexible" it is meant that the blood bag system is sufficiently pliable to collapse and allow the entire bag contents to empty. It is preferred that the blood bag be as flexible as possible but yet retain sufficient strength and temperature resistance to be functional. Modulus is an indicator of flexibility and it is preferred that the plastic material have a modulus in the film of no more than about 25,000 or 30,000 psi as determined by ASTM method D882 (tensile properties of film and sheeting). The plastic material more preferably has a modulus in the film of no more than about 20,000 psi with a modulus of no more than about 15,000 psi being most preferred.

Another factor related to flexibility, that is an important feature of a blood bag, is its "hand". Those in the health care industry are used to IV bags, or blood bags, that have a certain feel or "hand". This property can be related to the materials' stiffness or modulus. A bag that is too flexible is generally considered unsuitable due to a concern that the bag may not be strong or tough enough to avoid being ruptured during handling. However, if the bag is too rigid damage to the contents and proper drainage of the contents become a concern. This feature is not easily quantifiable and is simply a factor that needs to be considered when producing the final blood bag product.

By "hemocompatible" it is meant that the blood bag system (containing vitamin E, etc.) has the characteristic that it will not interact with the stored blood or other biological materials during storage and usage conditions in a way that will significantly lower the safety, purity or potency (efficacy) of the stored blood or its components or other biological materials. By "sterilizable" it is meant that the blood bag system is capable of withstanding autoclave (i.e. 121° C. for 30 minutes), ethylene oxide gas (ETO), radiation or other sterilization methods used to kill microorganisms without suffering significant adverse effects on the physical and/or chemical properties of the system or its biocompatibility. By "smooth" it is meant that the surface of the material is sufficiently even such that damage of blood components due to abrasion is minimized; however, if blood cells are not present this is not of particular importance. "Inert" refers generally to the same quality as hemocompatibility but is meant that the plastic material itself is essentially innocuous and does not, to any significant extent, react chemically with the blood. The blood bag should be sufficiently transparent or have sufficient contact clarity so that during typical use, a technician, nurse, physician or other person will be able to visibly identify the contents of the bag and identify pertinent blood characteristics including quality (particularly color) and quantity. This characteristic is, however, not absolutely required for the present invention, since there may be other acceptable methods of identifying the contents of the bag and its quality such as some form of color and/or freshness coding or marking.

Several different plastic materials have sufficient characteristics to be suitable for use in the present invention. It is envisioned that any plastic material that meets the above requirements of flexibility, hemocompatibility and sterilizability would be useful in the blood bag system of the present invention. Suitable classes of plastic materials include, for example, polyesters, copolyesters, polyolefins, and the like. More preferred plastic materials, however, are elastomeric copolyesters, more specifically copolyesterethers having a high melt strength and a fast crystallization rate.

The copolyesterethers according to the more preferred aspect of this invention are derived from a dicarboxylic acid component consisting essentially of 1,4-cyclohexanedicarboxylic acid or an ester forming derivative thereof such as dimethyl-1,4-cyclohexane-dicarboxylate. The diol component consists essentially of 1,4-cyclohexanedimethanol and polytetramethylene ether glycol. The copolyesterethers further comprise from about 0.1 to about 1.5 mole %, based on the acid or glycol component, of a polyfunctional branching agent having at least 3 carboxyl or hydroxyl groups.

Such a copolyesterether is disclosed in U.S. Pat. No. 4,349,469, the disclosure of which is incorporated herein by reference in its entirety. Such a preferred plastic material is comprised of copolyesterethers having an inherent viscosity of about 0.8 to about 1.5 comprising A. a dicarboxylic acid component consisting essentially of 1,4-cyclohexanedicarboxylic acid (or an ester forming derivative thereof) having a trans isomer content of at least about 70%, B. a glycol component consisting essentially of
(1) 1,4-cyclohexanedimethanol, and
(2) from about 15 to about 50 weight percent, based on the weight of the polyesterether, of poly(tetramethylene ether) glycol having a molecular weight of about 500 to about 1,100, and C. from about 0.1 to about 1.5 mole percent, based on the mole percent of the acid or glycol component, of a branching agent having at least three COOH or OH functional groups and from 3 to 60 carbon atoms, and said copolyester being characterized by having a die swell of between about −90° and about +100% and a minimum crystallization time of less than 2.5 minutes.

The inherent viscosity (I.V.) is an indicator of processability and is a number relatable to the composition and molecular weight of the polyester and is in deciliters per gram. It is determined by measuring the flow time of a solution of known polymer concentration and the flow time of a solvent-blank in a capillary viscometer and then calculating the I.V. by using the following equation:

$$\{\eta\}\,^{25°\,C.}_{0.50\%} = \frac{\ln \frac{t_s}{t_o}}{C}$$

$\{\eta\}$ 25° C. = Inherent viscosity at 25° C. at a 0.50% polymer concentration of 0.50 gm per 100 mil of solvent.

ln = Natural Logarithm
$t_s$ = Sample Flow Time
$t_o$ = Solvent minus blank flow time
C = Concentration of Polymer in Grams Per 100 ml of Solvent = 0.50

The die swell is expressed as a percent and is calculated as follows using a 0.1 inch diameter die.

Die swell, % =

$$\frac{\text{Diameter in inches of Extrudate at 6}'' - 0.1'' \times 100}{0.1 \text{ inch}}$$

If the extrudate is less than 0.1 inch in diameter, the die swell is then a negative number because there is no swell. If the extrudate is larger than 0.1 inch in diameter, the die swell is a positive number. A die swell of 0% therefore indicates no change in the size of the extrudate.

To decrease processing time it is highly desirable to use rapidly crystallizing polyesterethers. The rates of crystallization of copolyesterethers can be measured by determining the times ($t_p$) to reach the peak crystallization exotherm during crystallization at various temperatures. Typically, there exists a temperature at which $t_p$ is less than for any other temperature. This minimum value of $t_p$ can be used as a single parameter characterization of crystallization rate. The shorter the minimum crystallization time the faster the copolyesterether will crystallize.

In the above-described copolyesterether it is preferred that said 1,4-cyclohexanedicarboxylic acid have a trans isomer content of at least about 80%, said 1,4-cyclohexanedimethanol have a trans isomer content of at least about 60%, and the molecular weight of the polytetramethylene ether glycol be about 500 to 1,000.

It is also preferred that the polytetramethylene ether glycol of said copolyesterether be present in an amount of about 20% to 35% based on the total weight of copolyesterether, and that the branching agent of said copolyesterethers be trimellitic anhydride. Other preferred embodiments of said copolyesterether include a preferred die swell between about −50% and +50%; and a preferred minimum crystallization time less than about one minute, more preferably less than about one-half minute. It is also preferred that said copolyesterether additionally contain an effective amount of a phenolic antioxidant. A preferred effective amount of said phenolic antioxidant is about 0.1% to 1.0% based on the weight of the copolyesterether.

A preferred phenolic antioxidant is available from Ciba-Geigy under the trademark Irganox 1010. This additive is a tetrafunctional compound that also aids in thermal stability and about 0.2% is preferably present in the polymer.

An even more preferred plastic material is disclosed in U.S. Pat. No. 4,349,469 and can be described as being comprised of copolyesterethers having an inherent viscosity from about 0.8 to about 1.5 comprising A. a dicarboxylic acid component consisting essentially of 1,4-cyclohexanedicarboxylic acid (or an ester forming derivative thereof) having a trans isomer content of at least about 80%, B. a glycol component consisting essentially of
  (1) 1,4-cyclohexanedimethanol having a trans isomer content of at least about 60%, and
  (2) from about 20 to about 35 weight percent, based on the weight of the polyesterether, of poly(tetramethylene ether) glycol having a molecular weight of about 500 to about 1,000, and C. from about 0.1 to about 1.5 mole percent, based on the mole percent of the acid or glycol component, of a branching agent having at least three COOH or OH functional groups and from 3 to 60 carbon atoms, said copolyesterether being characterized by having a die swell of between about −90% and about +100% and a minimum crystallization time of less than about 2.5 minutes.

A suitable, preferred copolyesterether within the description above is available from Eastman Chemical Products, Inc., Kingsport, Tennessee, and is known by the trademark ECDEL.

Another preferred plastic material suitable for use in the present invention is a polyester of 1,4-cyclohexanedicarboxylic acid and 1,4-cyclohexanedimethanol modified with 10 to 30 mole percent dimer acid. Such a polyester is disclosed in U.S. Pat. No. 4,045,431, the disclosure of which is incorporated herein by reference in its entirety. Such a suitable plastic material disclosed in said patent can be described as being comprised of a polyester having an inherent viscosity of at least about 0.6, preferably at least about 0.7, a flexural modulus of about 30,000 psi or less and a melting point of at least about 140° C., the polyester being comprised of:

A. a dicarboxylic acid component which is
  (1) from about 90 to about 70 mole percent, preferably about 85 to about 75 mole percent, 1,4-cyclohexanedimethanol acid having a trans isomer content of at least about 90%, and
  (2) from about 10 to about 30 mole percent, preferably from about 15 to about 25 mole percent dimer acid, and B. 1,4-cyclohexanedimethanol having a trans isomer content of at least about 60%.

It is presently contemplated, though not preferred, that the plastic materials described above can have incorporated therein non toxic plasticizers such as acetyl tributyl citrate.

It is also presently contemplated, though not preferred, that the plastic material suitable for use in the blood bag of the present invention can be laminated (i.e., have two or more layers) wherein the individual plastic layers are of the same or different material. The presently preferred method of forming this layered material is by coextrusion, however, any conventional method of coextrusion or extrusion lamination is believed to be useful to make these materials.

Suitable coextruded structures include for example but are not limited to one or more layers of at least one polyolefin and/or polyolefin copolymer, one or more layers of at least one polyester such as an elastomeric copolyester and one or more layers of at least one adhesive such as one produced from a copolyester. A preferred coextruded layered structure would be copolyesterether/adhesive/polyolefin. These coextruded materials are less permeable than the single layer material but preferably have oxygen carbon dioxide permeabilities as described above.

The effective blood-stabilizing amount of vitamin E is that amount that produces an increase in blood or blood component stability in stored blood as compared to blood stored under identical conditions without vitamin E. An increase in blood stability means that the stored blood or blood component is better suited for clinical use (i.e. for infusing into patients) which for whole blood or red blood cells usually means that following storage they have less cell lysis and higher cell viability when compared with storage in a comparable blood container free of vitamin E. This improvement is generally manifest by reduced plasma hemoglobin content, reduced osmotic fragility and/or reduced hemolysis due to $H_2O_2$ challenge. Generally, a certain time period passes before the improved stability becomes manifest, typically at least about 14 days under normal storage conditions. Normal storage conditions are typically about atmospheric pressure and about 4° C.

A typical preferred effective amount of vitamin E is about 5 to about 100 mg per deciliter (dl = 100 ml) of whole blood; a more preferred effective amount is about 10 to about 50 mg per dl. Of course, when the vitamin E is added to the blood bag prior to introducing the blood, the effective amount of vitamin E is based upon the volume of blood that will later be introduced into the blood bag.

The vitamin E can be incorporated in concentrated form or added as solution in a suitable solvent, e.g. alcohol, at the desired concentration to the blood bag or at least one compartment thereof. It is also contemplated that the vitamin E can be incorporated into the plastic material directly, using conventional techniques, so that an effective amount of vitamin E will be in contact with the blood during storage.

It is believed that any method of incorporating the vitamin E into the blood bag system so as to increase the blood stability is suitable for the present invention. For example, the vitamin E can be present in the blood-containing compartment or can be stored in a second sealed compartment attached to the main body of the bag or the tubing and then added to the blood after blood collection.

Vitamin E is known to include several forms of alpha tocopherol. As used herein the term "vitamin E" refers to any form of vitamin E that exists (which includes esterified forms) or any combination thereof. One form of vitamin E is the d-alpha-tocopherol which is isolated from natural sources and consists solely of the naturally occurring stereoisomer RRR-alpha-tocopherol. Another form is the d,l-alpha-tocopherol also known as all racemic-alpha-tocopherol which is a mixture of 8 stereoisomers produced during its synthesis. In general, the naturally occurring d-alpha form and its esters are preferred over the synthetic forms due to the higher biological potency and the absence of synthetic stereoisomers which may impose stress upon the human body receiving the infusion of blood. It is preferred that the purity of the vitamin E exceed 97% and be essentially free of synthetic stereoisomers. Typical esters include alkyl esters such as $C_1$-$C_4$ alkyl esters (e.g., d-alpha-tocopheryl acetate, and succinate) and polyethylene glycol succinate.

We have also found that d-alpha-tocopherol (RRR-alpha-tocopherol) is surprisingly more effective in maintaining the integrity of the blood cells than are related forms of vitamin E, such as its acetate ester (depending upon the plastic material and its thickness). The blood bag of the present invention can be made using conventional techniques known in the art. The blood bag of the present invention can also be of any physical design known in the art. Examples of suitable blood bag designs are disclosed in U.S. Pat. Nos. 4,451,259; 4,286,597; 4,300,559; 4,301,800; 4,507,387; and 4,222,379, the disclosures of which are incorporated herein by reference in their entirety. A typical blood bag is equipped with access tubing and sealed access ports. If desired, the blood bag of this invention can be a multi-compartment system wherein a first compartment for holding blood or at least one blood fraction, and other compartments can contain other beneficial substances.

In addition to vitamin E, other beneficial substances can be added to the blood or be in the first or second compartments described above, or can be in one or more other compartments. The individual compartments can have one or more common walls or can be separate bags connected by tubing. It is important that the portion of the blood bag that is in contact with the blood during storage is made of the plastic material that is flexible, hemocompatible, and sterilizable and is substantially free of harmful blood extractables. The other parts of the blood bag, e.g., tubing and/or other compartments, can be made of the same material or of some other material suitable for that purpose.

The "other beneficial substances" described above can be anticoagulants/preservatives, nutrient additives, salts, minerals, antibiotics, or any other substance or a mixture thereof commonly used by medical or research personnel for use in conjunction with stored blood, fractions thereof, or stored biological materials. Examples of anticoagulants/preservatives commonly used in the trade are: CPD(citrate phosphate dextrose) and CPDA-1 (citrate phosphate dextrose adenine). An example of a nutrient additive is ADSOL which contains adenine, dextrose, mannitol and saline (available from Fenwal Laboratories). Ascorbic acid and its salts (vitamin C) have a sparing effect on the antioxidant activity of vitamin E in red blood cells. It is, therefore, envisioned that a combination of vitamins E and C can be used in the system. Similarly, other compounds with antioxidant activity such as beta-carotene, (vitamin A), etc. can also be included.

Blood to be stored in accordance with the present invention can be placed into the blood bag by any conventional means known in the art. The blood in the blood bag is then typically stored at about 4° C. for a desired period of time. Typically, blood is stored over 21 days up to 35 days at this temperature; however, it is possible to have suitable blood when stored up to 49 days when using the blood bag of this invention. Blood or suitable blood components can also be stored in these bags for extended periods in the freezer at temperatures of −20° to −196° C.; however, the blood bags of the present invention are particularly useful when storing blood and blood components that must be kept above freezing temperatures.

The present invention is contemplated as being useful for the storage of many biological solutions particularly blood and blood products. Suitable biological solutions include but are not limited to whole blood, red blood cells, platelets, plasma, cell cultures, and nutritional and medicinal biological solutions. The stored biological solutions that are benefited the most by the blood bags of the present invention are those that contain red blood cells and platelets. Red blood cells and platelets are known to require good oxygen and $CO_2$ exchange and are delicate and very susceptible to damage.

EXAMPLES

The following examples are to illustrate the present invention but should not be interpreted as a limitation thereon.

EXAMPLE 1

The following laboratory procedure describes the general laboratory method of preparing the copolyester ether used in the examples disclosed hereafter.

To a 500 ml round bottom flask fitted with a nitrogen purge, stirrer, and a distillate side arm are charged the following:

55.7 grams (0.278 moles) of t-dimethylcyclohexane dicarboxylate (DMCD)

0.25 grams (0.0013 moles of trimelletic anhydride (TMA)

0.20 grams of Irganox 1010 antioxidant stabilizer 25.1 grams (0.025 moles) of poly(tetramethyleneoxide glycol) (PTMG with molecular weight of 1000)

37.5 grams (0.260 moles) 1,4-cyclohexanedimethanol (CHDM)

100 ppm of Titanium (based on Acetyl isopropyl titanate)

The flask is immersed in a Belmont metal bath at 220° C. and the esterinterchange is carried out for 1 hour while the contents are being stirred under nitrogen purge. The temperature is then increased to 265° C. and a vacuum is slowly applied to the esterinterchange product. Vacuum levels of 0.3-0.1mm of mercury are reached after approximately 15 minutes. The vacuum is maintained for a period of 1 hour during which time the esterinterchange product undergoes polycondensation and there is a marked increase in melt viscosity. At the end of the 1 hour time period the metal bath heat source is removed and the contents of the flask are allowed to cool under a positive nitrogen pressure. The solidified contents are then removed from the flask.

The copolyester has the following properties: Inherent Viscosity of 1.23: "$R_d$" color of 70.0, "a" color of −1.0 and a "b" color value of 12.0. The polymer exhibits a melting point, as measured by differential scanning colorimeter of 195°–200° C.

The $R_d$, a, and b refer to the color scale and are defined or explained as follows: "$R_d$"—The measure of reflectance relative to the white color standard. Operationally, "$R_d$" is defined as 100 times the amount of light reflected by a specimen divided by the amount of light reflected by the reference standard.

"a"—Positive values of "a" indicate redness and negative values of "a" indicate greenness.

"b"—Positive values of "b" indicate yellowness and negative values of "b" indicate blueness.

A more detailed description of these terms is available in Method D2244 of the American Society for Testing Materials (ASTM).

EXAMPLE 2

The purpose of this example is to demonstrate the effectiveness of the blood bag system of the present invention.

Experimental conditions were as follows:

Blood was collected in accordance with recognized standards (as described in the Technical Manual of the American Association of Blood Banks) from 32 healthy volunteers from whom informed consent was obtained. 450 ml of venous blood was collected from each subject into copolyesterether blood bags (the copolyesterether is prepared according to U.S. Pat. No. 4,349,469 as described in the more preferred method above and is available from Eastman Chemical Products, Inc., under the trademark ECDEL and is the copolyester component used throughout the examples) containing standard level of CPD anticoagulant (63 ml per unit of blood). Blood units were centrifuged in an International Centrifuge-5000 with a Blood Bank rotor at 2350 RPM for 7.17 minutes, plasma was then removed, and the nutrient additive solution ADSOL (100 ml) was added. The final packed cell volume was approximately 70%. Using sterile technique, natural vitamin E (d-alpha-tocopherol) and d-alpha-tocopheryl acetate in three final concentrations of 5, 50, and 100 mg/dl were added. Four bags for each concentration for each form of vitamin E were used. Four control bags had no vitamin E added and four blood bags had ethanol alone added. Blood was stored at 4° C. for up to 49 days in a standard blood bank refrigerator (Puffer Hubbard #PH750) using conventional blood banking techniques. As an indicator of membrane loss or damage during storage, an osmotic fragility test was carried out using hypotonic sodium chloride (NaCl) solutions. Due to the difference in osmotic pressure inside and outside the blood cells created by the addition of hypotonic solution, water enters the red blood cells causing an increased pressure inside the cells. Cells that have weakened or damaged cell membranes rupture during this test releasing hemoglobin into the solution. Similar analytical conditions were used for all samples.

Results are summarized below in Table 1 for osmotic fragility for red blood cell storage. Blood was tested on days 0, 1, 14, 28, 35, 42, 45 and 49; however, for simplicity only results for day 35 are shown below, challenged with a hypotonic 0.65% NaCl solution. This length of storage was selected because it is the maximum storage time most commonly practiced in the industry. The data reported are representative of all data obtained and the conclusions from all the data are essentially the same. This same length of storage is used for all Examples. Data for bags with ethanol added (no vitamin E added) were also included in the corresponding control groups because ethanol had no effect on the parameters tested.

TABLE 1

Copolyester Plastic Material Approximately 10 mil Thick

| Form of Vitamin E Added | Amount of Vitamin E mg/dl | Percent Hemolysis of Red Blood Cells Challenged With a 0.65% NaCl Hypotonic Solution* |
|---|---|---|
| d-alpha-tocopherol | 0 | 38.4 |
|  | 5 | 40.3 |
|  | 50 | 35.5 |
|  | 100 | 34.5 |
| d-alpha-tocopheryl acetate | 0 | 40.5 |
|  | 5 | 34.6 |
|  | 50 | 27.8 |
|  | 100 | 27.9 |

*Additional concentrations of NaCl were used to determine the osmotic fragility of the blood; however, due to the volume of the data, only data for this concentration are presented. Data presented are deemed to be representative. The percent hemolysis is an indicator of osmotic fragility and was determined by analyzing the hemoglobin content of the solution.

As shown in Table 1 vitamin E reduced osmotic fragility of the blood cells stored in the inventive system by greater than 30% even though this thickness of copolyester material was not the most preferred. This conclusion was confirmed by regression analyses which indicated a statistically significant effect of vitamin E in the system.

Results with low levels of d-alpha-tocopherol are not inconsistent with the above conclusions. These results are within experimental error and the benefits of d-alpha-tocopherol are not as apparent at this thickness of plastic material.

EXAMPLE 3

The purpose of this example is to further confirm the results in Example 2 and to compare the thickness of the plastic material in the inventive vitamin E based system (using the copolyester as above). In this example, the copolyester thickness was approximately 5 mil. This thickness provided acceptable strength and other physical qualities required for storage of blood and its components.

Experimental conditions were as follows:

Following informed consent, 450 ml of venous blood was collected from three healthy volunteers in the copolyester blood bags containing CDP as an anticoagulant. The blood obtained from the three donors was then pooled in order to minimize the variation between red blood cells (i.e., vitamin E content, selenium, etc.). The blood units were centrifuged in an International Centrifuge 5000 with a blood bank rotor at 5000 RPM for 5 to 7 minutes. Plasma was expressed and discarded. (Note: ADSOL was not used in this example.)

Sheets of the copolyester plastic material were sealed by heat to form small "bags" in a fashion similar to blood storage bags. Into each small bag, 9.9 ml of packed red cells (70-80% hematocrit) was pipetted. d-alpha-tocopherol or d-alpha-tocopheryl acetate was dissolved in absolute ethanol (1% v/v) and 0.1 ml added to give a final concentration of 5, 50 or 100 mg/dl packed red cells, respectively. There were four replications per group and an equal number of controls to which no vitamin E was added. Each bag was sealed under a laminar flow hood by folding a portion of the top half and securing the fold with a sterile paper clip.

As in Example 2 an osmotic fragility test was used as an indicator of membrane loss during storage using hypotonic saline. The results are summarized in Table 2 below (only results for red blood cells stored for 35 days and challenged with a 0.65% NaCl solution are included for the reasons discussed in Example 2).

TABLE 2

| Copolyester Plastic Material Approximately 5 mil Thick | | |
|---|---|---|
| Form of Vitamin E Added | Amount of Vitamin E mg/dl | Percent Hemolysis When Challenged With a 0.65% NaCl Hypotonic Solution* |
| None (Control) | — | 17.1 |
| d-alpha-tocopherol | 5 | 7.2 |
| | 50 | 2.2 |
| | 100 | 3.0 |
| d-alpha-tocopheryl acetate | 5 | 10.4 |
| | 50 | 10.0 |
| | 100 | 10.6 |

*The lower overall hemolysis of Table 2 compared to Table 1 is thought to be due to the plastic material thickness, and in part to the difference in experimental conditions such as smaller blood samples with higher surface/volume of blood ratio and the absence of ADSOL.

Statistical analysis of the percent hemolysis results in Table 2 indicated that vitamin E was effective in reducing osmotic fragility of red blood cells stored in the inventive system. The results shown in Table 2 also indicate that the d-alpha-tocopherol was more effective than its acetate ester under the conditions of this experiment. These results showed that the system of the present invention based on the above defined copolyester with a thickness of approximately 5 mil plus 50 mg/dl of vitamin E in the alcohol form (d-alpha-tocopherol) was most effective in preserving the cell viability during storage.

EXAMPLE 4

The purpose of this example is to demonstrate that a blood bag of the present invention containing vitamin E using either a copolyester system as straight film or coextruded, is an effective blood bag.

Experimental conditions were as follows:

Following informed consent, 450 ml of venous blood was collected from each of seven healthy volunteers. Five mil thick copolyester film straight or coextruded (1 mil copolyester layer, 0.5 mil adhesive tie layer and 3.5 mil propylene/ethylene copolymer layer) was formed into medium small bags using heat sealing. Twenty five ml of packed red blood cells (75-80% hematocrit) were stored with CPD as anticoagulant and ADSOL as the nutrient additive. Vitamin E additive consisted of 50 mg/dl of either d-alpha-tocopherol, d-alpha-tocopheryl acetate, a 1:1 mixture of these two forms, or d,l-alpha-tocopherol. Replications were 15 each for copolyester and coextruded copolyester. Results for red blood cells stored for 35 days are summarized in Table 3 below.

TABLE 3

| Vitamin E | Partial $CO_2$ Pressure mm Hg | pH | Percent Hemolysis When Challenged with a 0.65% NaCl Hypotonic Solution | Plasma Hemoblogin mg % |
|---|---|---|---|---|
| Copolyester, 5 mil (Not CoExtruded) | | | | |
| d-alpha-tocopherol | 42 | 6.76 | 15 | 700 |
| d-alpha-tocopherol acetate | 49 | 6.77 | 20 | 730 |
| d,l-alpha-tocopherol | 42 | 6.80 | 17 | 740 |
| d-alpha-tocopherol + d-alpha-tocopherol acetate | 49 | 6.67 | 21 | 1480 |
| Copolyester, 5 mil (CoExtruded)[a] | | | | |
| d-alpha-tocopherol | 72 | 6.63 | 20 | 760 |
| d-alpha-tocopherol acetate | 76 | 6.61 | 15 | 600 |
| d,l-alpha-tocopherol | 81 | 6.67 | 15 | 760 |
| d-alpha-tocopherol + d-alpha-tocopherol acetate | 69 | 6.63 | 13 | 600 |

[a] Made of about 1 mil copolyester (as above), about 0.5 mil adhesive tie layer (a commercial adhesive identified as ADMER AT469 from Mitsui Company), and about 3.5 mil polypropylene/ethylene copolymer (identified as TENITE polyallomer 361A from Eastman Chemical Products, Inc.).

It was concluded from the data above, that the coextruded copolyester in combination with several sources of Vitamin E performed well for blood storage.

EXAMPLE 5

The purpose of this example is to demonstrate the effect of the form of vitamin E (alcohol versus ester) and its interaction with the thickness of the plastic material (straight and coextruded) used in the present invention.

Experimental conditions were as follows:

Following informed consent, 450 ml of venous blood was collected from seven healthy volunteers. Other conditions were as described in Example 4 except: copolyester bags, both from straight and coextruded material, were tested at 2 thicknesses namely 5 and 10 mil (5 mil as in (a) in Example 4 above and 10 mil using 8.5 mil of propylene/ethylene copolymer instead of 3.5 mil). CPD was used as anticoagulant but the nutrient solution ADSOL was not used. Vitamin E forms tested were: d-alpha-tocopherol and its ester d-alpha-tocopheryl acetate at 50 mg/dl. Results are summarized below in Table 4 for red blood cells stored for 35 days.

In addition to some of the parameters measured earlier, the hemolysis resulting from hydrogen peroxide challenge was measured in order to determine the effect of each form of vitamin E in protecting red blood cells from damage due to peroxides. The red blood cells are subject to peroxide damage when in storage or after infusion.

TABLE 4

| Material | Vitamin E | Partial $CO_2$ Pressure mm Hg | pH | Percent Hemolysis Due To $H_2O_2$ Challenge |
|---|---|---|---|---|
| Copolyester (Not CoExtruded) | | | | |
| 5 Mil | d-alpha-tocopherol | 57 | 6.99 | 4 |
| 5 Mil | d-alpha-tocopherol acetate | 51 | 6.99 | 16 |
| 10 Mil | d-alpha-tocopherol | 70 | 7.02 | 7 |
| 10 Mil | d-alpha-tocopherol acetate | 71 | 7.03 | 8 |
| Copolyester (Coextruded) | | | | |
| 5 Mil$^{(a)}$ | d-alpha-tocopherol | 94 | 6.87 | 6 |
| 5 Mil$^{(a)}$ | d-alpha-tocopherol acetate | 89 | 6.94 | 23 |
| 10 Mil$^{(b)}$ | d-alpha-tocopherol | 81 | 6.99 | 5 |
| 10 Mil$^{(b)}$ | d-alpha-tocopherol acetate | 85 | 6.95 | 24 |

$^{(a)}$As in Table 3.
$^{(b)}$As in (a) except instead of 3.5 mil polypropylene/ethylene copolymer, there is 8.5 mil.

The results in Table 4 show surprising interactions on the effect of different forms of vitamin E (alcohol versus acetate). Specifically in the non coextruded copolyester, the alcohol form reduced the hemolysis from hydrogen peroxide challenge over the acetate form in the 5 mil thickness but not in the 10 mil thickness. In the coextruded copolyester, the alcohol form reduces the hemolysis due to $H_2O_2$ challenge for both thicknesses.

The unexpected interactions between vitamin E forms and plastic material were apparent in the earlier examples although in some cases the differences may have been partially masked by additional interactions with the nutrient solution and other additives. It should also be noted that the hydrogen peroxide test was not performed in all examples.

While the present invention has been described in detail, variations and modifications can be made without departing from the reasonable scope thereof.

We claim:

1. A blood storage system essentially free of blood extractables that are harmful to the human body comprising: a plastic container characterized as being flexible, hemocompatible, sterilizable, having an oxygen permeability of at least 100 PU and a carbon dioxide permeability of at least about 800 PU; and an amount of vitamin E to stabilize blood stored therein, said amount being at least 5 mg per dl blood, wherein said plastic container has sufficient oxygen and carbon dioxide permeabilities to be effective in blood storage in combination with said vitamin E.

2. The blood storage system of claim 1 wherein said vitamin E is selected from d-alpha-tocopherol, d-alpha-tocopheryl acetate, d-alpha-tocopheryl succinate and mixtures thereof and said amount of vitamin E is that amount sufficient to cause blood stored in said blood bag to exhibit an improvement in at least one of the following properties when compared to blood stored in a comparable blood container free of vitamin E; reduced plasma hemoglobin content, reduced osmotic fragility, and reduced hemolysis due to $H_2O_2$ challenge.

3. The blood storage system of claim 2 wherein said plastic container is made of a plastic material that has a modulus in the film of no more than 30,000 psi is inert, smooth, translucent or transparent and is selected from the group consisting of at least one of copolyesters, polyesters, and polyolefins.

4. The blood storage system of claim 3 wherein said vitamin E is d-alpha-tocopherol present in an amount of about 5 to 100 mg per dl blood and said plastic material is between about 3 and 15 mil thick and has an oxygen permeability of at least 250 PU and a carbon dioxide permeability of at least 2,500 PU.

5. The blood storage system of claim 4 wherein said amount of vitamin E is about 10 to about 50 mil per dl blood, and said plastic material is an elastomeric copolyester and is between about 5 and 10 mg thick.

6. The blood storage system of claim 1 wherein said plastic material is a copolyesterether having an inherent viscosity of about 0.8 to 1.5 comprising:
   A a dicarboxylic acid component consisting essentially of 1,4-cyclohexanedicarboxylic acid having a trans isomer content of at least about 70%,
   B. a glycol component consisting essentially of
      (1) 1,4-cyclohexanedimethanol, and
      (2) about 15 to about 50 weight percent, based on the weight of the polyesterether, of polytetramethylene ether glycol having a molecular weight of about 500 to about 1,100, and
   C. about 0.1 to about 1.5 mole percent, based on the mole percent of the acid or glycol component, of a branching agent having at least three COOH or OH functional groups and from 3 to 60 carbon atoms, said copolyesterether being characterized by having a die swell between about −90% and about +100% and a minimum crystallization time of less than about 2.5 minutes.

7. A blood storage system comprising: a plastic container essentially free of blood extractables harmful to the human body comprised of a flexible, hemocompatible, sterilizable, smooth, inert, translucent or transparent elastomeric copolyester between about 2 and 60 mils thick having a modulus in the film of no more than 30,000 psi, an oxygen permeability of at least about 250 PU, and a carbon dioxide permeability of at least about 2,500 PU and contained therein about 5 to 100 mg per dl volume of vitamin E.

8. The blood storage system of claim 7 wherein said amount of vitamin E is 10 to 50 mg per dl volume of d-alpha-tocopherol and said elastomeric copolyester is between about 3 and 15 mil thick and is a copolyesterether having an inherent viscosity of about 0.8 to about 1.5 comprising:
- A. a dicarboxylic acid component consisting essentially of 1,4-cyclohexanedicarboxylic acid having a trans isomer content of at least about 80%,
- B. a glycol component consisting essentially of
  - (1) 1,4-cyclohexanedimethanol having a trans isomer content of at least about 60%, and
  - (2) from about 20 to about 35 weight percent, based on the weight of the polyesterether, of polytetramethylene ether glycol having a molecular weight of about 500 to about 1,000, and
- C. from about 0.1 to about 1.5 mole percent, based on the mole percent of the acid or glycol component, of trimellitic anhydride, said copolyesterether being characterized by having a die swell of between about −50% and about +50% and a minimum crystallization time of less than about one minute.

9. The blood storage system of claim 8 wherein said blood stored system additionally contains a beneficial amount of at least one of the following: vitamin C, anticoagulants, nutrients, salts, minerals, antibiotics, or mixtures thereof and said copolyesterether forming said plastic container is about 5 mil thick and additionally contains an effective amount of a phenolic antioxidant.

10. A method for storing blood comprising placing at least one blood fraction in contact with an effective blood stabilizing amount of vitamin E in a blood bag essentially free of blood extractables that are harmful to the human body comprised of a flexible, hemocompatible, sterilizable plastic material having an oxygen permeablity of at least about 100 pu and a carbon dioxide permeability of at least about 800 pu wherein said amount of vitamin E is at least 5 mg per dl blood.

11. The method of claim 10 wherein said plastic material has a modulus in the film of no more than 30,000 psi is also smooth, inert, translucent or transparent, and is selected from copolyesterethers, polyesters, and polyolefins; and said vitamin E is present in an amount of about 5 to 100 mg per dl blood and is selected from d-alpha-tocopherol, d-alpha-toco-pheryl acetate, d-alpha-tocopherol succinate and mixtures thereof.

12. The method of claim 11 wherein said vitamin E is present in a concentration at about 10 to 50 mg per dl blood and said plastic material has an oxygen permeability of at least 250 PU and a carbon dioxide permeability of at least about 2,500 PU, is between about 5 and 40 mils thick and is a copolyesterether having an inherent viscosity of about 0.8 to about 1.5 comprising:
- A. a dicarboxylic acid component consisting essentially of 1,4-cyclohexanedicarboxylic acid having a trans isomer content of at least about 70%,
- B. a glycol component consisting essentially of
  - (1) 1,4-cyclohexanedimethanol, and
  - (2) from about 15 to about 50 weight percent, based on the weight of the polyesterether, of polytetramethylene ether glycol having a molecular weight of about 500 to about 1,100, and
- C. from about 0.1 to about 1.5 mole percent, based on the mole percent of the acid or glycol component, of a branching agent having at least three COOH or OH functional groups and from 3 to 60 carbon atoms, said copolyesterethers being characterized by having a die swell between about −90% and about +100% and a minimum crystallization time of less than about 2.5 minutes.

13. The method of claim 12 wherein said vitamin E is d-alpha-tocopherol and said plastic material is about 5 mil thick.

14. A composition suitable for preparing blood bags comprising: an effective blood stabilizing amount of vitamin E and a flexible, sterilizable, hemocompatible copolyesterether material essentially free of blood extractables that are harmful to the human body having a modulus in the film of no more than about 30,000 psi and an oxygen permeability of at least about 250 PU, and a carbon dioxide permeability of at least about 2,500 PU wherein said amount of vitamin E is at least 5 mg per dl blood.

15. The composition according to claim 14 wherein said copolyesterether has an inherent viscosity of about 0.8 to 1.5 and comprises:
- A. a dicarboxylic acid component consisting essentially of 1,4-cyclohexanedicarboxylic acid having a trans isomer content of at least about 70%,
- B. a glycol component consisting essentially of
  - (1) 1,4-cyclohexanedimethanol, and
  - (2) from about 15 to about 50 weight percent, based on the weight of the polyesterether, of polytetramethylene ether glycol having a molecular weight of about 500 to about 1,100, and
- C. from about 0.1 to about 1.5 mole percent, based on the mole percent of the acid or glycol component, of a branching agent having at least three COOH or OH functional groups and from 3 to 60 carbon atoms, said copolyesterethers being characterized by having a die swell between about −90% and about +100% and a minimum crystallization time of less than about 2.5 minutes.

16. The method according to claim 10 wherein said blood fraction is a blood product that contains blood cells.

17. A blood storage system essentially free of blood extractables that are harmful to the human body comprising: a plastic container made of a plastic material selected from copolyesters, polyesters, and polyolefins between about 3 and 15 mils thick characterized as being inert, smooth, translucent or transparent, flexible, hemocompatible, sterilizable, having an oxygen permeability of at least 250 pu, and a carbon dioxide permeability of at least 2,500 pu; and about 5 to 100 mg per dl blood of d-alpha-tocopherol.

18. The blood storage system of claim 17 wherein said plastic material is a copolyester material about 5 mil thick.

19. A blood storage system essentially free of blood extractables that are harmful to the human body comprising: a plastic container comprised of a plastic material characterized as being flexible, hemocompatible, and sterilizable, having an oxygen permeability of at least 100 PU and a carbon dioxide permeability of at least about 800 PU; and an amount of vitamin E to stabilize blood stored therein, said amount being at least 5 mg per dl blood, wherein said plastic container has the proportional oxygen and carbon dioxide permeabilities as a 5 ml thickness of said plastic material, said permeabilities being sufficient for said container to be effective in blood storage in combination with said vitamin E.

20. The blood storage system of claim 19 wherein said plastic material has an oxygen permeability of at least 250 PU and a carbon dioxide permeability of at least 2,500 PU.

* * * * *